United States Patent
Biedermann et al.

(10) Patent No.: US 6,918,308 B2
(45) Date of Patent: Jul. 19, 2005

(54) SENSOR DEVICE, IN PARTICULAR FOR A PROSTHESIS, AND PROSTHESIS HAVING SUCH A SENSOR DEVICE

(75) Inventors: Lutz Biedermann, Villingen (DE); Wilfried Matthis, Weisweil (DE)

(73) Assignee: Biedermann Motech GmbH, Vs-Schwenningen (DE)

( * ) Notice: Subject to any disclaimer, the term of this patent is extended or adjusted under 35 U.S.C. 154(b) by 84 days.

(21) Appl. No.: 10/213,327

(22) Filed: Aug. 6, 2002

(65) Prior Publication Data

US 2003/0029247 A1 Feb. 13, 2003

(30) Foreign Application Priority Data

Aug. 10, 2001 (DE) .......................................... 101 39 333

(51) Int. Cl.$^7$ ............................................... G01L 1/40
(52) U.S. Cl. ............................................... 73/862.629
(58) Field of Search .......................... 73/862.629, 796, 73/862.625, 862.626, 862.627, 862.632

(56) References Cited

U.S. PATENT DOCUMENTS

| | | |
|---|---|---|
| 2,520,923 A | 9/1950 | Franzel et al. |
| 4,282,762 A | 8/1981 | Zenker |
| 4,640,138 A | 2/1987 | Meyer et al. ............ 73/862.04 |
| 5,197,488 A | 3/1993 | Kovacevic |
| 5,336,854 A | 8/1994 | Johnson |
| 5,391,844 A | 2/1995 | Johnson et al. |
| 5,456,724 A | 10/1995 | Yen et al. |
| 5,888,212 A | 3/1999 | Petrofsky et al. |
| 5,894,094 A * | 4/1999 | Kuchler et al. ......... 73/862.044 |
| 6,253,626 B1 * | 7/2001 | Shoberg et al. ......... 73/862.044 |
| 6,539,804 B1 * | 4/2003 | Iwata ....................... 73/504.13 |

FOREIGN PATENT DOCUMENTS

| | | |
|---|---|---|
| DE | 35 16 234 A1 | 11/1986 |
| DE | 297 23 632 U1 | 2/1999 |
| DE | 198 59 931 | 7/2000 |
| GB | 2 096 777 A | 10/1982 |
| WO | WO 99/04235 | 1/1999 |
| WO | WO 00/38599 | 7/2000 |

OTHER PUBLICATIONS

Sanders, et al., "Measurement of Stresses in Three Orthogonal Directions at the Residual Limb–Prosthetic Socket Interface", 8434 IEEE Transactions on Rehabilitation Engineering, Jun. 1, 1993, No. 2, New York, pp. 79–85.

* cited by examiner

*Primary Examiner*—Max Noori
(74) *Attorney, Agent, or Firm*—George W. Neuner; Edwards & Angell LLP

(57) ABSTRACT

A sensor device (15) for a prosthesis, in particular for a leg prosthesis, is provided for measuring forces acting on the prosthesis, having a ring-shaped outer member (16) of closed construction and an inner member (21, 22) connecting two opposite inner sides (17a, 17b) of the outer member having a sensor element (31) for measuring the force acting in the direction of the connecting axis. The outer member deforms under the action of a bending moment while the inner member (21) feels only the axial force acting in the direction of its connecting axis. By this means measurement of the axial force unaffected by bending moments is possible. Furthermore, the sensor device is able to transmit loads.

18 Claims, 3 Drawing Sheets

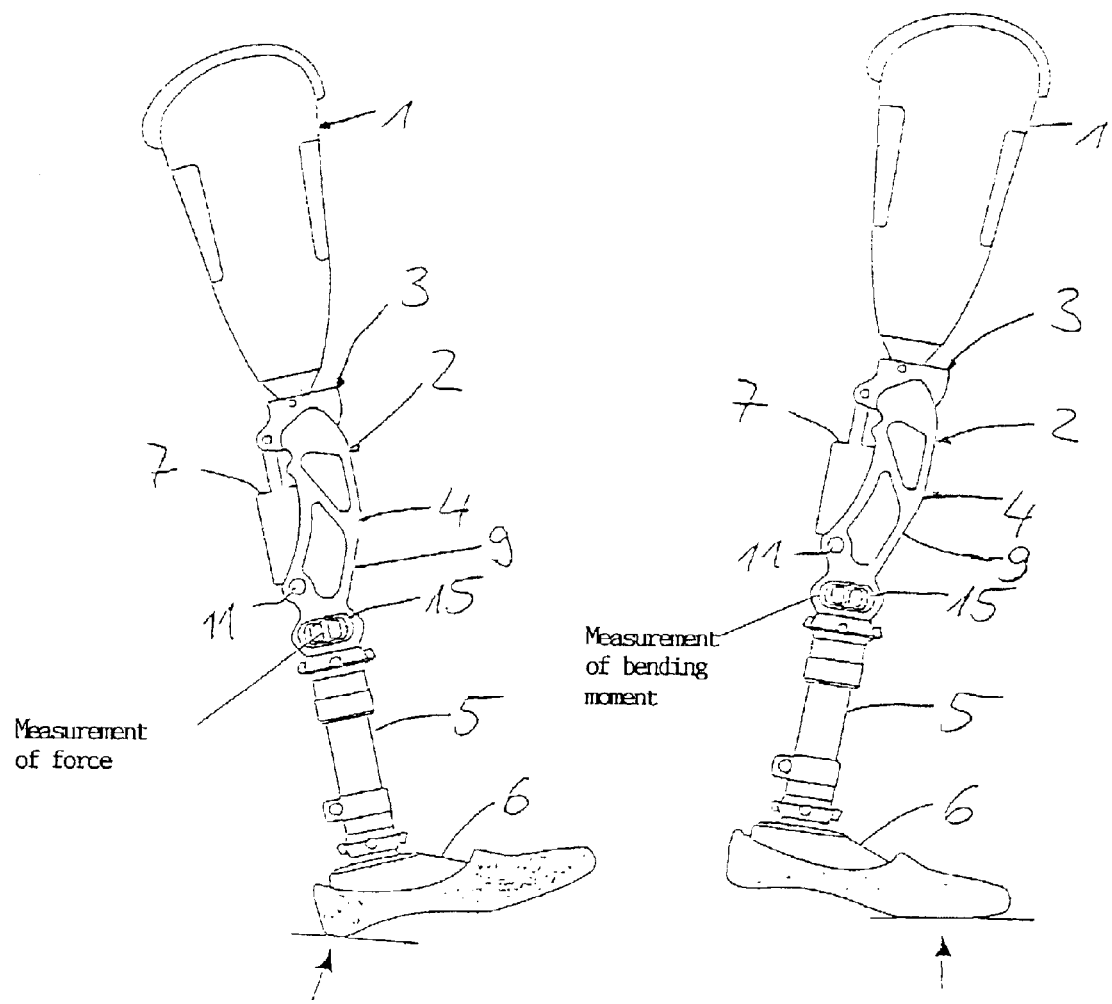

Figure 6:
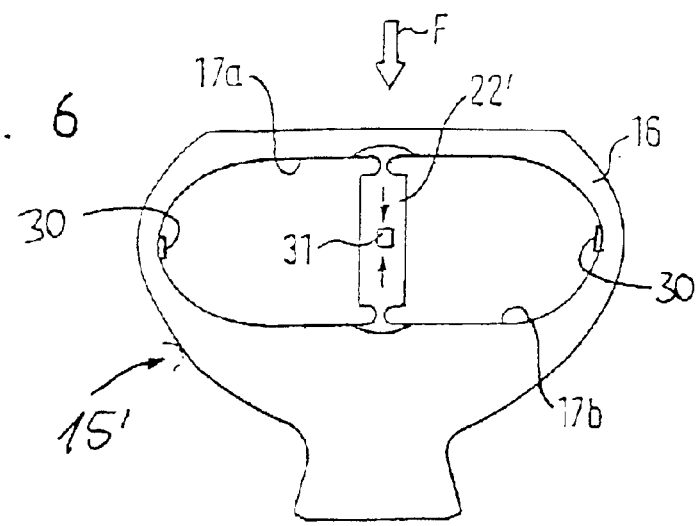

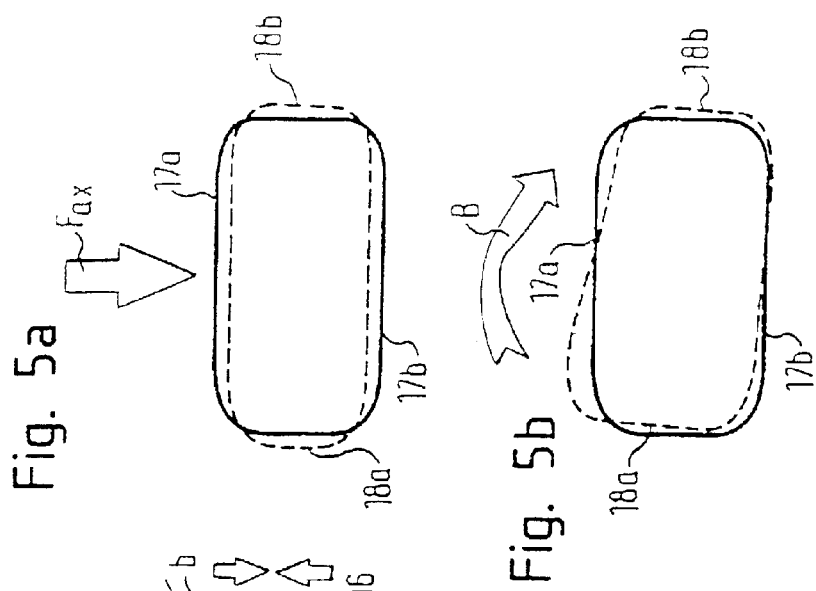
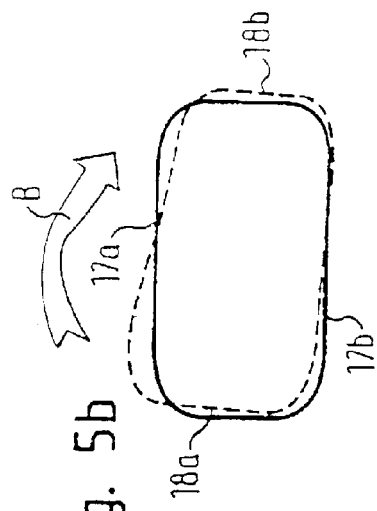
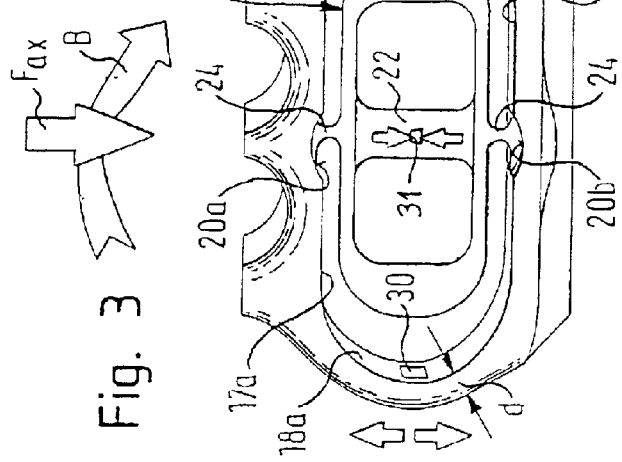
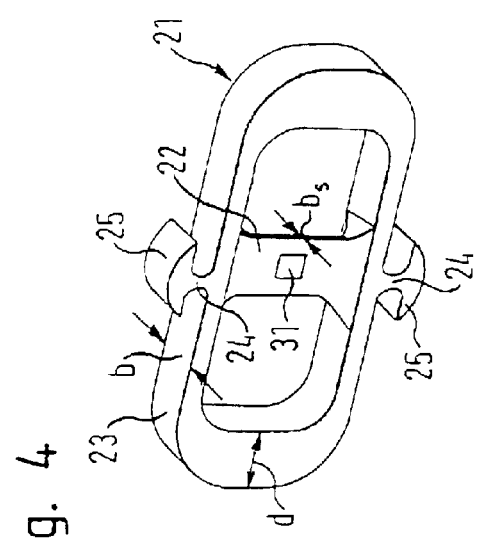
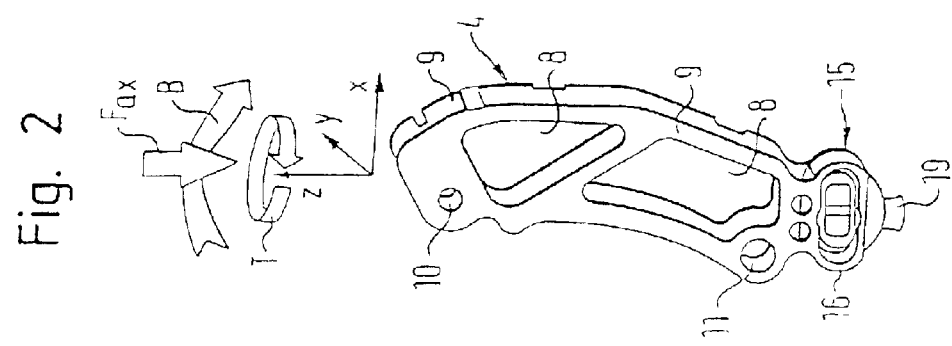

SENSOR DEVICE, IN PARTICULAR FOR A PROSTHESIS, AND PROSTHESIS HAVING SUCH A SENSOR DEVICE

The invention relates to a sensor device, in particular for a prosthesis and preferably for a leg prosthesis, and a prosthesis having a sensor device of this type.

In mechanical prosthesis systems it must be ensured that even under extreme load conditions or when walking actively no component of the prosthesis fails due to cyclical overloading. This gives rise to a difficulty for the prosthesis designer to the extent that the range of loads to be taken into consideration in the design of the prosthesis is very wide and partial load components are only inadequately known. Since, however, the overall structural length, weight and volume are critical design factors, most components of the prosthesis are designed in lightweight construction, ie most parts of the prosthesis, in particular the prosthesis carrier, are designed only for a certain number of operating cycles.

In the case of electronically controlled prostheses further problems arise since the weight due to battery components and active components for controlling movement are added, as a result of which the requirements on the materials used are further increased. Additionally, a sensor unit for measuring the ground reaction force for ambulatory analysis is necessary. In most cases such a sensor includes the measurement of axial forces and bending moments. At the same time there is a technical problem to the effect that the expansions due to axial force which amounts to a maximum of approximately 1,500 N are less by a factor of approximately 5 to 10 than the expansions due to bending moments which are approximately 150 Nm. Since, however, each expansion sensor, such as a wire strain gauge, Hall sensor or capacitance sensor by way of example, senses both expansions as a combination an optimum mechanical design is necessary for resolving the loads. This is rendered more difficult by the low axial forces and by additional load components, such as for example lateral bending moments and torsional moments. Furthermore, a high expansion with respect to the axial force is necessary in order to achieve a stable zero point.

WO 00/38 599 discloses an electronically controlled leg prosthesis having an upper leg section and a lower leg section and a knee joint connecting the two in which force sensors for measuring the total force acting on the prosthesis are provided in region of the sole of the foot. In this prosthesis force sensors are further provided for measuring the total force or also the bending force in the shin-bone section. The measurement of the total force, however, is not independent of effects from bending moments.

It is an object of the invention to provide a sensor device, in particular for a prosthesis and preferably for a leg prosthesis, and a prosthesis of this type having such a sensor device in which the loads to be expected are reliably transmitted and precise measurement is possible.

This task is solved by a sensor device according to claim 1 or 14 or by a prosthesis having such a sensor device as claimed in claim 13.

Refinements of the invention are specified in the subsidiary claims.

The sensor device according to the invention has the advantage that loads on the prosthesis are reliably transmitted by the sensor device. Furthermore, there is the advantage of resolution of axial and bending loads. Due to the resolution of loads the walking phases in a leg prosthesis of stepping onto the ground, rolling from heel to toe and lifting can be precisely determined. Moreover, there is a stable zero point independent of the environment, ie temperature fluctuations or forces exerted during assembly, by screws for example. Accordingly, there is no sensor drift.

Further characteristics and practical features of the invention emerge from the description of exemplified embodiments with reference to the figures.

The figures show:

FIGS. 1(a)–(b) a leg prosthesis with the sensor device according to the invention in different ambulatory positions;

FIG. 2 a perspective view from the side of a first embodiment of a sensor device in a shin-bone section of a leg prosthesis together with a system of coordinates;

FIG. 3 an enlarged lateral perspective view of the sensor device;

FIG. 4 an enlarged illustration in perspective of an inner part of the sensor device in FIG. 3;

FIGS. 5(a)–(b) a schematic illustration of the deformation of the sensor device under different loads;

FIG. 6 a schematic illustration of another embodiment of the sensor device; and

Figure 7:
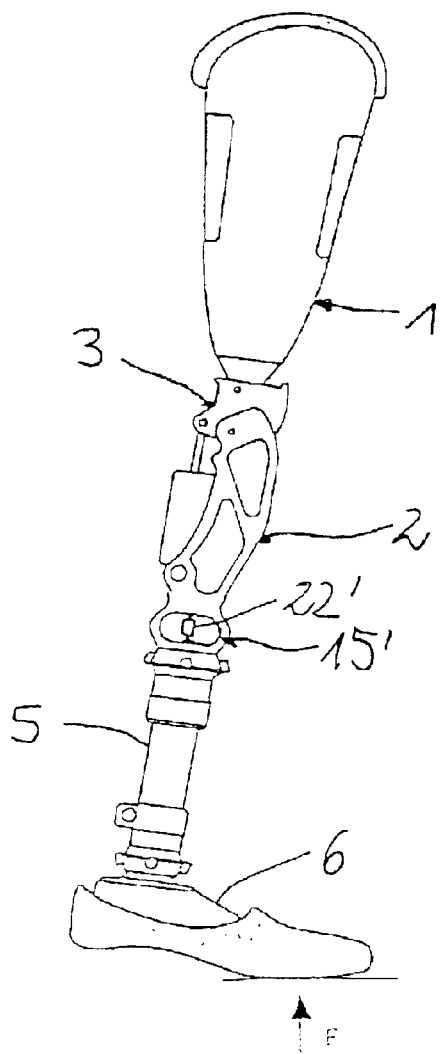

FIG. 7 a schematic illustration of another embodiment of the leg prosthesis.

As may be seen in FIGS. 1(a) and 1(b) a leg prosthesis comprises in known manner an upper leg part 1, a lower leg part 2 and a knee joint 3 connecting the two. The lower leg part 2 possesses a shin-bone part 4 with a lower leg tube 5 and a foot part 6 connected to the latter. The foot part 6 possesses in known manner a leaf spring, which is not illustrated in the figures, to allow a springy step. The upper leg part 1 is constructed for connection to a leg stump. The artificial knee joint 3 contains a damping member in the form of a piston-and-cylinder device 7.

As may be seen in FIGS. 1(a), 1(b) and 2 the shin-bone section 4 is constructed from two elongated side sections 9 running parallel to one another provided with hollowed sections 8 for purposes of weight-saving which at their end facing towards the upper leg part 1 have bores 10 for accommodating a swivel axis of the artificial knee joint 3 and in their end facing away from the upper leg part 1 have corresponding openings 11 for connection to the piston-and-cylinder device 7. At their end facing away from the upper leg part 1 the side parts 9 are connected via a sensor device 15. In the embodiment shown the side parts 9 and the sensor device are constructed in one part.

In FIG. 2 a rectangular coordinate system for the prosthesis and the forces occurring is further shown. In this case the z-axis runs in the direction of a connecting axis between the upper leg part 1 and the shin-bone section 4 in the extended position of the prosthesis passing through the swivel axis of the artificial knee joint. The x-axis and the z-axis define a swivel plane of the artificial knee joint.

As is evident from FIGS. 2 to 4, the sensor device 15 consists of a substantially oval, ring-shaped outer member 16 having a width b in the y-direction, that is perpendicular to the to the swivel plane, which is approximately equal to the distance between the side parts 9 of the shin-bone section. The longitudinal sides 17a, 17b of the oval ring are aligned in the x-direction perpendicular to the z-axis. The side parts 9 of the shin-bone section 4 extend at opposite edges of one of the longitudinal sides 17a of the oval ring towards the upper leg part. The short lateral sections of the oval ring form webs 18a, 18b having a predetermined thickness d. On the inner sides facing towards the oval interior of the outer member 16 of the longitudinal sides 17a, 17b two furrow-shaped recesses 20a, 20b located opposite one another and extending over the entire width of the ring are provided centrally which serve to accommodate an inner member described below. On its longitudinal side 17b facing away from the side parts 9 of the shin-bone section 4 the sensor device has a conically tapering section having a projection 19 for connecting to the lower leg tube 5.

The outer member 16 is formed of a material which is lightweight and in the ring shape shown exhibits desirable elasticity under the action of axial forces acting in the direction of the z-axis and bending forces acting in the swivel plane. The outer member is constructed of aluminium for example. The thickness d of the ring is selected so that the deformations under load required for measuring the forces occur.

On the sides of the webs 18a, 18b facing towards the interior space sensor elements 30 are provided in this exemplified embodiment at positions opposite one another to detect any bending moment B in the swivel direction of the prosthesis illustrated in FIG. 2 by the curved arrow. The sensor elements are constructed by way of example in the form of wire strain gauges.

As may be seen in FIGS. 3 and 4, the sensor device further possesses an inner member 21 arranged in the interior of the oval ring of the outer member 16 for detecting the axial force $F_{ax}$ acting in the z-direction which is illustrated by the straight arrow in FIG. 2. The inner member 21 consists of a sensor part 22 of web-shaped construction having a substantially rectangular cross-section on which a sensor element 31, a wire strain gauge by way of example, is fitted. In the exemplified embodiment shown the sensor part 22 forms a connecting web provided centrally between the inner sides of the longitudinal sides of a substantially rectangular ring 23. The outer and inner edges of the rectangle are rounded off. The width b of the ring 23 in the y-direction is distinctly smaller than that of the outer member 16. As is evident in particular in FIG. 4 the width $b_s$ of the sensor part 22 in the y-direction is smaller than that of the ring 23. Advantageously, the width $b_s$ of the sensor part 22 is approximately a quarter to a third of the width b of the ring 23. By this means the sensor part 22 possesses a small cross-section which allows optimum measurement of the axial force $F_{ax}$. The thickness d of the ring on the short sides is greater than that on the long sides as a result of which the short sides form compensation members for relieving bending of the sensor part 22. The thickness d of the short sides, the width of the ring and its diameter are chosen in such a way that due to the mass of the member so formed a desired bending relief corresponding to the bending moment expected to occur is obtained.

On the outer sides of the longitudinal sides at points facing away from the sensor part 22 the ring 23 possesses web-shaped projections 24 extending outwardly over the width b of the ring 23 on whose free end a section 25 in the shape of a segment of a cylinder is formed whose dimensions are such that it fits into the furrow-shaped recesses 20a, 20b of the outer part. The thickness of the webs 24 in the x-direction is smaller than that of the sensor part 22 in order to afford a small area of action for bending moments and hence to keep the transmission of bending forces in the z-x plane as small as possible. Ideally the thickness of the web-shaped projections 24 is such that a punctiform connection to the outer member 16 having no or low moment is obtained. Such a connection prevents or minimises secondary effects on the axial force due to superimposed bending moments. Furthermore, the length of the webs 24 is chosen so that the inner member composed of the ring 23 and the sensor part 22 can be inserted exactly into the outer member 16. The inner member is constructed of the same material as the outer member in order to avoid stresses due to temperature as far as possible. In the assembled state the inner member is inserted into the furrow-shaped recesses 20a, 20b of the outer member and firmly connected to it at this point, eg by gluing or welding. In this way the sensor part 22 is aligned in the z-direction of the prosthesis and the longitudinal sides of the outer member 16 and the ring 23 of the inner member are parallel.

In operating the prosthesis when walking, as shown in FIGS. 1(a) and 1(b), or when operating the prosthesis in test mode, the forces or force components illustrated in FIG. 2 act by the foot part taking a step. On the one hand, there is the axial force $F_{ax}$ acting in the z-direction on the sensor part 22 aligned in the z-direction and, on the other hand, a bending moment B. A torsional moment T with respect to the z-axis plays almost no role on account of the ring-shaped construction of the outer part 16 since the oval ring is torsionally rigid. The same applies to lateral bending moments in the y-direction. As is evident from FIGS. 5(a) and 5(b) the axial force or force components $F_{ax}$ result in shortening and widening of the oval ring of the outer part 16 and hence in a measurable change in the length of the sensor part 22 which is detected by the sensor 31. The bending moment B occurring results in shortening or compressive strain of one lateral web 18b of the outer part and in elongation of the opposite web 18a which is detected by the sensors 19 provided on the inner sides of the webs 18a, 18b. The bending moment is determined by the difference between the recorded values. As shown in FIG. 5(b), however, the bending moment B results in no measurable change in length of the sensor part 22 so that the axial force occurs without being affected by the bending moment. On account of the described construction of the outer part 16 the latter is so stable that the principal load acting on the prosthesis is transmitted through it.

Any bending moments nevertheless transmitted through the webs 24 of the inner member 21 are intercepted due to the construction of the inner member in the form of a ring 23 around the sensor part 22, since this member exhibits flexural rigidity. Thus, the ring 23 of the inner member having the widened short sides acts as flexural relief for the sensor part 22. The thickness of the widened sides and hence their mass are selected as a function of the flexural relief needed.

Thus, using the sensor device described above measurement of the axial force without any influence from bending moments is possible. The resolution of loads occurring due to the sensor device according to the invention allows the precise measurement of the relatively small deformations due to the axial force. In this way various ambulatory phases such as stepping onto the ground, rolling from heel to toe and lifting the foot part can be determined.

In the embodiment described above the outer and inner members are described as two parts which can be joined together and fixedly connected to one another. However, the sensor device 15 may also be constructed in one part, eg as a machined or cast part. Conversely, the sensor device need not be constructed in one part with the shin-bone section 4, but rather can also be connected via a suitable fastening device, eg bolts, to the shin-bone section.

In the modified embodiment shown in FIG. 6 the sensor device 15' is similar to the sensor device 15, wherein, however, the inner member is formed only from the web 22' without a ring 23 being provided. This suffices in principle since the outer member 16 already absorbs the bending moment. A leg prosthesis having such a sensor device 15' is shown in FIG. 7. The bending moment can be measured via sensors provided on the insides of the webs 18a, 18b as in the case of the embodiment shown in FIG. 3.

In another modified embodiment the sensors 30 are not present on the insides of the webs 18a, 18b, rather the bending moment is measured by separate sensors provided on the lower leg tube 5 or below the knee joint 3 at a different point from the sensor device 15' in the shin-bone section 2.

The sensors 30, 31 need not be constructed as wire strain gauges but can rather be piezoelectric or Hall sensors or other sensors.

In another modified embodiment the oval ring of the outer member is constructed in the form of a rectangle. The expression ring-shaped or ring as used in connection with this invention in the description and the claims both for the outer member and the inner member is not restricted, however, to a circular, oval, rectangular or polygonal ring but rather encompasses any closed structure in which the thickness and width of the structure in relation to the enclosed space are such that the described deformation results under the action of a bending moment.

What is claimed is:

1. A sensor device constructed to be located between two parts having a connecting axis between the two parts, the sensor device having a closed, ring-shaped outer member for connecting the two parts, the ring-shaped member having first and second opposing inner sides; an inner member connecting only the first and second opposing inner sides of the outer member; and a first sensor element located on the inner web member for measuring the force acting in the direction of the connecting axis between the two parts.

2. The sensor device according to claim 1, wherein the ring-shaped outer member has a first inner size across the ring along the connecting axis and a second inner size across the ring at the position perpendicular to a direction of the first inner size and at a longitudinal center of the inner member along the connecting axis, the first inner size being smaller than the second inner size.

3. The sensor device according to claim 1, wherein the ring-shaped outer member has third and fourth opposing inner sides in a direction perpendicular to the direction of the connecting axis, the sensor device further comprising a second sensor element positioned on one of the third and fourth opposing inner sides for measuring a force acting on the outer member outside of a longitudinal axis of the inner web member.

4. The sensor device according to claim 1, wherein the inner member comprises a web member bearing the sensor element and a further structural component for flexural relief of the web member.

5. The sensor device according to claim 1, wherein the ring-shaped outer member forms an oval ring having a center, the first and second sides opposing each other along a shortest distance across the oval through its center, and the inner member comprises a web member connecting the first and second inner sides of the oval ring to one another.

6. The sensor device according to claim 1, wherein the ring-shaped outer member forms a rectangular ring and the inner member comprises a central web, the sensor element being provided on the central web.

7. The sensor device according to claim 1, wherein the inner member has a first cross-section at the sensor element and the ring-shaped outer member has a second cross-section at a point of action of a force in the direction of the connecting axis, the first cross-section being smaller than the second cross-section.

8. The sensor device according to claim 1, further comprising second and third sensor elements provided on the ring shaped outer member and arranged symmetrically with respect to the connecting axis for determining a bending moment acting on the outer member.

9. The sensor device according to claim 1, wherein ring-shaped outer member and the inner member are fixedly connected to one another.

10. The sensor device according to claim 1, wherein the ring-shaped outer member and the inner member are formed from the same material.

11. The sensor device according to claim 1, wherein one of said two parts is a lower leg part of a leg prosthesis and the sensor device is provided on the lower leg part.

12. The sensor device according to claim 2, wherein the ring-shaped outer member forms an oval ring having a center, the first and second sides opposing each other along a shortest distance across the oval through its center, and the inner member comprises a web member connecting the first and second inner sides of the oval ring to one another.

13. A prosthesis comprising a sensor device according to claim 1.

14. The prosthesis according to claim 13, wherein the prosthesis is a leg prosthesis.

15. A sensor device for measuring mechanical forces, the sensor device comprising:

a sensor section, a force sensor located on the sensor section for measuring a first force ($F_{ax}$) acting on the sensor section in a first direction; and a flexural relief section connected to the sensor section, the flexural section being structured and arranged in such a manner that, under the action of a second force acting in a second direction, the flexural relief section is deformed in such a manner that the sensor section remains substantially unaffected by the second force.

16. The sensor device according to claim 15, wherein the flexural relief section is further structured and arranged in such a manner that it absorbs a bending moment (B) acting additionally to the force ($F_{ax}$) acting in the first direction so that the sensor section remains substantially unaffected.

17. The sensor device according to claim 15, wherein the flexural relief section further comprises possesses at least one sensor element for measuring the bending moment (B).

18. The sensor device according to claim 15, wherein the sensor device comprises an outer ring-shaped member and an inner member, wherein the inner member comprises the sensor section and the ring-shaped outer member comprises the flexural relief section.

* * * * *